United States Patent [19]

Caldwell

[11] Patent Number: 4,568,510
[45] Date of Patent: Feb. 4, 1986

[54] METHOD AND SYSTEM FOR URANIUM EXPLORATION

[75] Inventor: Richard L. Caldwell, Dallas, Tex.

[73] Assignee: Mobil Oil Corporation, New York, N.Y.

[21] Appl. No.: 484,391

[22] Filed: Apr. 12, 1983

Related U.S. Application Data

[63] Continuation-in-part of Ser. No. 189,267, Sep. 22, 1980.

[51] Int. Cl.⁴ ............................................. G01N 23/12
[52] U.S. Cl. .................................... 376/154; 376/164; 250/269
[58] Field of Search ................. 250/269; 376/154, 164

[56] References Cited

U.S. PATENT DOCUMENTS

| | | | |
|---|---|---|---|
| 3,686,503 | 8/1972 | Givens et al. | 250/269 |
| 3,828,189 | 8/1974 | Givens | 376/164 |
| 4,180,727 | 12/1979 | Givens | 250/269 |
| 4,180,729 | 12/1979 | Givens | 250/269 |
| 4,180,730 | 12/1979 | Givens et al. | 250/269 |
| 4,280,048 | 7/1981 | Smith | 376/164 |
| 4,350,887 | 9/1982 | Barnard et al. | 250/269 |
| 4,379,229 | 4/1983 | Givens | 250/269 |
| 4,388,266 | 6/1983 | Givens | 376/164 |

*Primary Examiner*—Sal Cangialosi
*Attorney, Agent, or Firm*—A. J. McKillop; Michael G. Gilman; George W. Hager, Jr.

[57] ABSTRACT

A portable uranium analyzer employs a neutron source and a neutron detector for carrying out an uranium assay along the surface of the earth and a gamma ray detector for carrying out a natural gamma radiation assay along the surface of the earth. The neutron source irradiates the underlying earth formation along an exploration line in either a continuous scan mode or in a plurality of fixed assay points. Prompt or delayed neutrons resulting from neutron fission of any uranium present in the formation are detected and recorded during assaying. The uranium assay and the natural gamma radiation assay are correlated to identify formations suspected of containing uranium.

5 Claims, 2 Drawing Figures

METHOD AND SYSTEM FOR URANIUM EXPLORATION

This is a continuation-in-part of U.S. Patent Application Ser. No. 189,267, filed Sept. 22, 1980.

BACKGROUND OF THE INVENTION

Natural gamma-ray exploration for uranium is carried out as a qualitative indicator of uranium mineralization in an earth formation. A high gamma-ray count rate suggests a mineralized region, but cannot always be used as a reliable quantitative measure of uranium ore grade. This is due primarily to conditions of disequilibrium which exist between the parent uranium-238 and the daughter elements, especially bismuth-214, which emit the bulk of gamma-rays contributing to the natural gamma-ray activity. Disequilibrium has been found to exist when the radioactive daughter elements, through various processes such as leaching, become separated from the parent uranium. If sufficient time has not elapsed between the separation of the uranium parent and the radioactive daughter elements, a relatively low gamma-ray activity may be present at the actual ore body. On the other hand, one can find high natural radioactivity coming from the separated daughter with little or no uranium present.

In addition to the above, other elements, particuarly potassium and thorium, emit natural gamma radiation. This radiation, when detected and recorded, reduces the effectiveness of natural gamma radiation activity as a quantitative measure of uranium ore grade.

One current exploration practice is to drill exploration holes on a widely separated pattern and on a closer pattern after a good show of mineralization is found from natural gamma-ray activity. Core samples are taken from the drilled holes and extensively assayed chemically to quantitatively evaluate the ore deposit. This practice, however, is very expensive. For example, the costs of coring a hole and chemically assaying the cores may be as much as seven to ten times the cost of the exploration hole. Moreover, the presently used technology misses many uranium ore bodies because all natural gamma-ray anomalies suggestive of ore grade mineralization cannot be confirmed because of the prohibitive costs of coring and chemical assaying.

Another current exploration practice is to drill an exploration hole after a good show of mineralization is found from measurement of surface natural gamma-ray activity and run a neutron fission log in the drilled hole. Natural earth formations may be characterized with regard to their uranium content on the basis of neutrons resulting from neutron fission of uranium. When a formation containing an uranium ore is irradiated with neutrons, the uranium nuclei react to neutron bombardment by breaking into smaller nuclear fractions which normally are referred to as fission products. The fission or uranium is attended by the emission of prompt neutrons immediately upon occurrence of the fission reaction and also by the emission of delayed neutrons subsequent to the fission process. The delayed neutrons are emitted by the fission products for an appreciable length of time following the fission reaction.

In U.S. Pat. No. 3,686,503 to Givens et al, there is disclosed a borehole logging system for characterizing the uranium content of natural earth formations surrounding a borehole on the basis of measurements of delayed neutrons resulting from neutron fission of uranium. In U.S. Pat. No. 4,180,730 to W. R. Mills, Jr., there is disclosed a borehole logging system for characterizing such uranium content on the basis of measurements of prompt neutrons resulting from neutron fission of uranium. In both cases the natural earth formations surrounding the borehole are irradiated with repetitive bursts of fast neutrons and, subsequent to each burst and after dissipation of the original source neutrons, delayed and prompt fission neutrons are detected as indications of uranium content of such formations.

SUMMARY OF THE INVENTION

In accordance with the present invention, there is provided a method for carrying out a reconnaisance survey over an extended area of the earth's surface for identifying zones suspected of containing ore deposits. The earth's surface is traversed along at least one line of survey with a neutron source, a neutron detector, and a gamma ray detector.

More particularly, the neutron source is operated periodically to irradiate the earth formations underlying the line of survey with repetitive bursts of fast neutrons spaced by time intervals greater than the time required for dissipation of neutrons originating in such bursts. During the time intervals between such bursts, and after the time required for dissipation of neutrons originating in such bursts, the neutron detector is operated to detect fission neutrons attendant to the presence of uranium in the earth formations. The gamma ray detector measures natural gamma radiation along the line of survey simultaneous with the neutron fission assay.

The neutron fission and natural gamma radiation assays are correlated at corresponding points along the line of survey to identify the presence of any uranium. A low gamma radiation measurement and a high neutron fission count rate identifies the presence of a surface uranium deposit in which the uranium daughter products are out of equilibrium with the parent uranium. A high gamma radiation measurement and a low neutron fission count rate identifies a subsurface uranium deposit in which the uranium daughter products are out of equilibrium with the parent uranium. A high gamma radiation measurement and a high neutron fission count rate identifies the presence of a surface uranium deposit in which the daughter products are in equilibrium with the parent uranium.

DESCRIPTION OF THE PREFERRED EMBODIMENT

Figure 1:
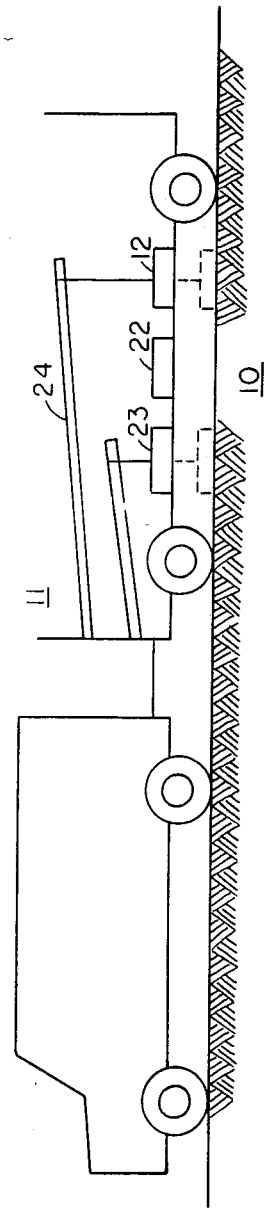
FIG. 1 illustrates a system for assaying along the earth's surface for subsurface uranium ore deposits.
Figure 2:
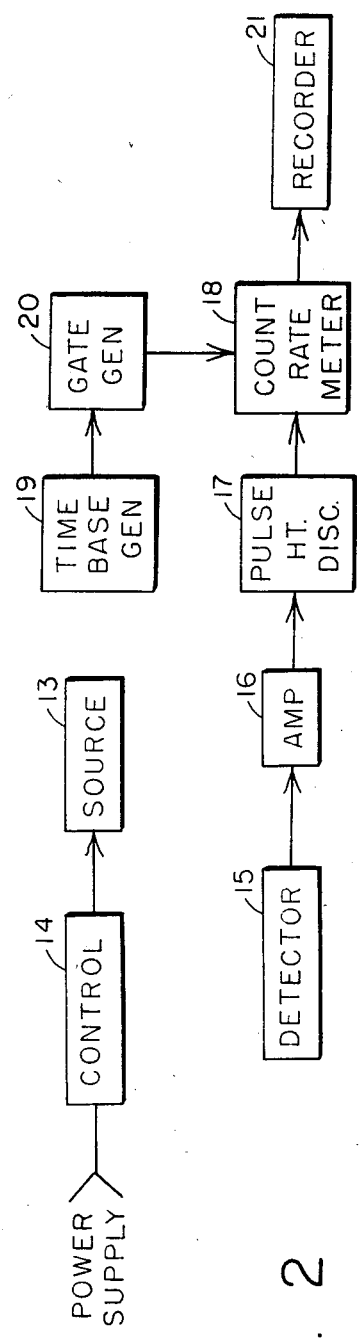
FIG. 2 is a schematic diagram of the uranium ore analyzer of the system of FIG. 1.

Referring to FIG. 1, a portion of a subsurface formation to be investigated or assayed for uranium content is shown at 10. It is traversed horizontally along the earth's surface by a vehicle 11 carrying a portable surface uranium analyzer 12. In one embodiment the analyzer 12 includes a neutron source 13, for irradiation of the formation 10 with bursts of fast neutrons, a control unit 14 for the source, and a radiation detector 15 for the detection of secondary radiation attendant to prompt or delayed neutrons resulting from neutron fission of uranium. The source 13 is preferably an accelerator-type, 14-Mev source which comprises a neutron generator tube and portable power supplies to operate the tube.

The output of the neutron generator tube is a burst of fast neutrons spaced in time for irradiation of the formation 10. A source of this type is the Kaman 3041 tube with high neutron output ($10^8$ neutrons/sec.) manufactured by Kaman Nuclear Corp. of Colorado Springs, Colo.

In theory the radiation detector 15 may be either a neutron detector or a gamma ray detector responsive to gamma rays atendant to the capture of thermal neutrons. However, the use of a gamma ray detector would require that complex energy level discrimination be carried out in order to discriminate the capture gamma rays from gamma rays resulting from the natural radioactivity of any uranium present and gamma rays resulting from the activation of oxygen-16 present. Thus it is preferred that the radiation detector 15 take the form of a thermal neutron detector. For example, detector 15 may comprise one or more helium-3 proportional counters of the type described in U.S. Pat. No. 3,102,198 to Bonner. These helium-3 counters are responsive primarily to thermal neutrons and become increasingly nonresponsive to neutrons of progressively higher energy levels.

The source 13 is operated cyclically to produce time-spaced bursts of fast neutrons, with the time intervals between the fast neutron bursts being greater than the time required for the dissipation within the formation 10 of the source neutrons. During the time intervals between the bursts and after dissipation of the source neutrons, the detector 15 is operated in conjunction with suitable gating controls to detect thermalized neutrons resulting from either prompt or delayed neutron fission of uranium. The output from detector 15 is applied by way of amplifier 16 and pulse height discriminator 17 to the gated count rate meter 18. Pulse height discriminator 17 is adjusted to pass to the count rate meter 18, those pulses produced by detector 15. Trigger pulses from a time base generator 19 are applied to delay the gate generator 20 which produces gating pulses for the duration of the desired prompt or delayed fission thermal neutron counting period. For prompt neutrons this period preferably begins about 50 to 100 microseconds after each neutron burst and extends until the beginning of the next neutron burst. For delayed neutrons, this period preferably begins about 2 to 5 milliseconds after each neutron burst and extends until the beginning of the next neutron burst. These gating pulses are applied to the count rate meter 18 for enabling the counting of neutrons during the preferred counting period. The output of count rate meter 18 is applied to recorder 21 as a representation of the uranium concentration in the formation 10.

The foregoing described portable uranium analyzer 12 is used in accordance with the present invention to run an uranium assay reconnaisance survey. This survey may be carried out by having the vehicle 11 traverse the surface of formation 10 while the analyzer 12 operates in a continuous scan mode. A particularly suitable linear velocity for the analyzer 12 along the earth's surface is in the range of 10 to 20 feet/minute. At this velocity the number of fast neutron bursts from source 13 is within the range of 30 to 60 bursts per linear foot for the delayed fission neutron mode and in the range of 3000 to 6000 bursts per linear foot for the prompt fission neutron mode. After completion of the survey the rcording thus obtained is examined in order to locate uranium ore bearing zones in formation 10 as indicated by the neutron count from count rate meter 18. The uranium bearing zone can be delineated in more detail an with more accuracy by additional survey lines run at 5 feet/minute.

In the alternation, the survey may be carried out on a point-to-point basis, that is, the analyzer 12 is moved to successive fixed points along the earth's surface and the assay carried out for a fixed period of time at each such fixed point. The assay period at each such point may be, for example, in the range of from just a few seconds to a few minutes each.

The assay record from either the continuous scan mode or the fixed point mode may be contoured to the surface of formation 10 to identify areas of subsurface economic deposits of uranium. Further, more expensive exploration efforts, such as borehole logging and coring, may be concentrated in the anomalous areas. Certainly, if there is some upward migration of uranium from ore deposits to the near surface rocks and soil (e.g. 1 or 2 feet depth) the assay operation of the present invention will provide an efficient means of uranium ore detection.

To achieve good assay statistics (i.e., high neutron counting rate) the analyzer 12 needs to be near the earth's surface, preferably within one foot. Accordingly, the analyzer may be lowered from the vehicle 11 toward the earth's surface in order to carry out the fixed point assay operation. In some instances, it may even be desirable to embed the analyzer in the earth's surface before making radiation measurements..

It may further be desirable to carry out a natural gamma radiation asay in addition to the neutron fission assay. In this case, a gamma ray detector 23 is also moved along the earth's surface by the vehicle 11 or some other suitable means. It may also be lowered toward the earth's surface in order to carry out the assay operation. If the gamma ray detector 23 is located on the same vehicle with the analyzer 12 and the gamma radiation assay run at the same time as the neutron fission assay, the gamma-ray detector should be preferably spaced from the neutron source 13 by a distance of eight feet or more in order to ensure that it is responsive only to natural gamma radiation. In addition, or in lieu thereof, measurements of the Radon-222 concentration in the formation 10 may be carried out by conventional radon emanometry techniques.

Such additional natural gamma ray or Radon-222 measurements may be correlated with the fission neutron assay. For purposes of example, the gamma ray measurement may be correlated in the following manner with the neutron fission assay to identify uranium concentration in the formation 10:

1. Low gamma radiation and a high neutron fission count rate may indicate the presence of a surface uranium deposit in which the daughter products are out of equilibrium with the parent uranium. For uranium, equilibrium occurs after about 250,000 years of undisturbed deposition and is governed by the decay rate of the longest lifetime uranium parent.

2. High gamma radiation and a low neutron fission count rate may indicate the presence of a subsurface uranium deposit out of equilibrium.

3. High gamma radiation and a high neutron fission count rate may indicate the presence of a surface uranium deposit in equilibrium. If there is a net high gamma radiation after correction for the surface uranium deposit, the presence of a subsurface uranium deposit could be indicated.

4. Low gamma radiation and a low neutron fission count rate is inconclusive of the presence of a subsurface uranium deposit.

A low gamma radiation would be about a one to five times increase over the natural background gamma radiation of the earth when little or no uranium is present. A high gamma radiation would be an increase in excess of about five times the natural background gamma radiation of the earth when little or no uranium is present.

A low neutron fission count rate for a delayed fission neutron count would be about a one to two times increase in delayed neutrons over the oxygen background of the earth, while a low neutron fission count rate for a prompt fission neutron count would be about a one to three times increase over the background measurement for a 0.005 weight % $U_3O_8$ content. High neutron fission count rates for delayed and prompt fission neutron count rates would be increases in excess of such low neutron fission count rate limits respectively.

The foregoing has described the uranium assay operation of the present invention. It is to be understood that various modifications to the disclosed embodiment, as well as alternative embodiments, may become apparent to one skilled in the art without departing from the scope and spirit of the invention as hereinafter defined by the appended claims.

What is claimed is:

1. A method of carrying out a reconnaisance survey over an extended area of the earth's surface for identifying zones suspected or containing uranium ore deposits, comprising the steps of:
   (a) traversing the earth's surface along at least one line of survey with a neutron source and a neutron detector,
   (b) periodically operating said neutron source to irradiate the earth formations underlying said line of survey with repetitive bursts of fast neutrons spaced by time intervals greater than the time required for dissipation of neutrons originating in said bursts,
   (c) during time intervals between said bursts and after the time required for dissipation of neutrons originating in said bursts operating said neutron detector to detect fission neutrons attendant to the presence of uranium in the earth formations,
   (d) recording radiation detected in step (c) to obtain a neutron fission assay record delineating said line of survey whereby zones of interest over an extended area of the earth's surface suspected of containing uranium ore may be identified,
   (e) carrying out a natural gamma radiation assay along said line of survey simultaneously with said neutron fission assay,
   (f) correlating said neutron fission assay with said gamma radiation assay at corresponding points along the line of survey,
   (g) identifying the presence of a surface uranium deposit in which the uranium daughter products are out of equilibrium with the parent uranium when there is a gamma radiation measurement of a one-to-five-times increase over the natural background gamma radiation of the earth with no uranium present and a neutron fission count rate for delayed neutrons of at least a two-times increase in delayed neutrons over the oxygen background of the earth or at least a three-times increase in prompt neutrons over the background measurement for a 0.005 weight % $U_3O_8$ content,
   (h) identifying the presence of a subsurface uranium deposit in which the uranium daughter products are out of equilibrium with the parent uranium when there is a gamma radiation measurement of at least a five-times increase over the natural background radiation of the earth with no uranium present and a neutron fission count rate for delayed neutrons of a one-to-two-times increase in delayed neutrons over the oxygen background of the earth or for prompt neutrons of a one-to-three-times increase in prompt neutrons over the background measurement for a 0.005 weight % $U_3O_8$ content, and
   (i) identifying the presence of a surface uranium deposit in which the uranium daughter products are in equilibrium with the parent uranium when there is a gamma radiation measurement of at least a five-times increase over the natural background radiation of the earth with no uranium present and a neutron fission count rate for delayed neutrons of a one-to-two-times increase in delayed neutrons over the oxygen background of the earth or for prompt neutrons of a one-to-three-times increase in prompt neutrons over the background measurement for a 0.005 weight % $U_3O_8$ content.

2. The method of claim 1 wherein said natural gamma radiation assay is spaced from said neutron fission assay such that said natural gamma radiation assay is unaffected by fast neutrons generated during said neutron fission assay.

3. The method of claim 1 wherein the depth of irradiation of the earth formations underlying said line of survey is in the order of one to two feet.

4. The method of claim 1 wherein a surface uranium deposit is in the order of one to two feet below the earth's surface.

5. The method of claim 1 wherein a subsurface uranium deposit is in excess of about two feet below the earth's surface.

* * * * *